US010859500B2

(12) United States Patent
Wei et al.

(10) Patent No.: US 10,859,500 B2
(45) Date of Patent: Dec. 8, 2020

(54) SURFACE PLASMON-MEDIATED CHEMICAL DEPOSITION AND PLASMONIC STRUCTURES

(71) Applicant: University of Florida Research Foundation, Inc., Gainesville, FL (US)

(72) Inventors: Wei David Wei, Gainesville, FL (US); Jingjing Qiu, Daly City, CA (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 0 days.

(21) Appl. No.: 16/093,152

(22) PCT Filed: Apr. 17, 2017

(86) PCT No.: PCT/US2017/027927
§ 371 (c)(1),
(2) Date: Oct. 12, 2018

(87) PCT Pub. No.: WO2017/184504
PCT Pub. Date: Oct. 26, 2017

(65) Prior Publication Data
US 2019/0178801 A1    Jun. 13, 2019

Related U.S. Application Data

(60) Provisional application No. 62/324,400, filed on Apr. 19, 2016.

(51) Int. Cl.
*G01N 33/553* (2006.01)
*G01N 21/65* (2006.01)
*B82Y 20/00* (2011.01)
*B01J 19/12* (2006.01)
*B82Y 30/00* (2011.01)
*B82B 3/00* (2006.01)
*B82Y 15/00* (2011.01)

(52) U.S. Cl.
CPC .......... *G01N 21/658* (2013.01); *B01J 19/127* (2013.01); *B82Y 20/00* (2013.01); *G01N 33/553* (2013.01); *B82B 3/00* (2013.01); *B82Y 15/00* (2013.01); *B82Y 30/00* (2013.01)

(58) Field of Classification Search
CPC ............................ G01N 21/658; B01J 19/127
See application file for complete search history.

(56) References Cited

U.S. PATENT DOCUMENTS 6,579,721 B1    6/2003  Natan et al.
7,733,481 B1 *  6/2010  Bratkovski .......... G01N 21/658
                                                356/301
(Continued)

OTHER PUBLICATIONS

Jingjing Qiu, "Surface Plasmon Mediated Chemical Solution Deposition of Gold Nanoparticles on a Nanostructured Silver Surface at Room Temperature", 2012 American Chemical Society (Year: 2012).*

(Continued)

*Primary Examiner* — Maurice C Smith
(74) *Attorney, Agent, or Firm* — Thomas Horstemeyer, LLP (57) ABSTRACT

Embodiments of the present disclosure provide plasmonic structures, methods of making plasmonic structures, and the like.

13 Claims, 9 Drawing Sheets

(56) References Cited

U.S. PATENT DOCUMENTS

| | | | |
|---|---|---|---|
| 2006/0034729 | A1 | 2/2006 | Poponin |
| 2011/0166045 | A1 | 7/2011 | Dhawan et al. |
| 2017/0045456 | A1* | 2/2017 | Fabris ............... G01N 21/658 |
| 2017/0168048 | A1 | 6/2017 | Szmacinski et al. |

OTHER PUBLICATIONS

Rongchao Jin, "Photoinduced Conversion of Silver Nanospheres to Nanoprisms" 2001 Science Nov. 30 (Year: 2001).*

Michael Fedoruk "Nanolithography by Plasmonic Heating and Optical Manipulation of Gold Nanoparticles" 2013 American Chemical Society (Year: 2013).*

Huabin Zhang,"Surface-Plasmon-Enhanced Photodriven CO 2 Reduction Catalyzed by Metal—Organic-Framework-Derived Iron Nanoparticles Encapsulated by Ultrathin Carbon Layers",Mar. 22, 2016,Adv. Mater (Year: 2016).*

Andrew McGrath, "Gold over Branched Palladium Nanostructures for Photothermal Cancer Therapy", 2015 American Chemical Society (Year: 2015).*

International Search Report and Written Opinion in International Application No. PCT/US17/27927 dated Jul. 20, 2017, 13 pages.

Qiu et al., "Surface Plasmon-Mediated Chemical Solution Deposition of Cu Nanoparticle Films", The Journal of Physical Chemistry, vol. 120, Issue 37 (2016) 20775-20780.

Lee et al., "Particle-Film Plasmons on Periodic Silver Film over Nanosphere (AgFON): A Hybrid Plasmonic Nanoarchitecture for Surface-Enhanced Raman Spectroscopy", ACS Applied Materials & Interfaces, vol. 8, Issue 1 (2015) 634-642.

Du, J. L.; Chen, Z. F.; Ye, S. R.; Wiley, B. J.; Meyer, T. J. "Copper as a Robust and Transparent Electrocatalyst for Water Oxidation", Angewandte Chem. Int. Ed. 2015, 54, pp. 2073-2078.

Kowalska, A. A.; Kaminska, A.; Adamkiewicz, W.; Witkowska, E.; Tkacz, M. "Novel Highly Sensitive Cu-Based SERS Platforms for Biosensing Applications", Journal of Raman Spectroscopy, 2015, 46, pp. 428-433.

Zhao, J.; Tran, P. D.; Chen, Y.; Loo, J. S. C.; Barber, J.; Xu, Z. J. "Achieving High Electrocatalytic Efficiency on Copper: A Low-Cost Alternative to Platinum for Hydrogen Generation in Water", ACS Catalysis 2015, 5, pp. 4115-4120.

Chan, G. H.; Zhao, J.; Hicks, E. M.; Schatz, G. C.; Van Duyne, R. P. "Plasmonic Properties of Copper Nanoparticles Fabricated by Nanosphere Lithography". Nano Letters 2007, 7, pp. 1947-1952.

Duan, J. L.; Cornelius, T. W.; Liu, J.; Karim, S.; Yao, H. J.; Picht, O.; Rauber, M.; Muller, S.; Neumann, R. "Surface Plasmon Resonances of Cu Nanowire Arrays", J. Phys. Chem. C 2009, 113, pp. 13583-13587.

Susman, M. D.; Feldman, Y.; Vaskevich, A.; Rubinstein, I. "Chemical Deposition and Stabilization of Plasmonic Copper Nanoparticle Films on Transparent Substrates", Chemistry of Materials 2012, 24, pp. 2501-2508.

Lu, S. C.; Hsiao, M. C.; Yorulmaz, M.; Wang, L. Y.; Yang, P. Y.; Link, S.; Chang, W. S.; Tuan, H. Y. "Single-Crystalline Copper Nano-Octahedra", Chemistry of Materials 2015, 27, pp. 8185-8188.

Ensafi, A. A.; Jafari-Asl, M.; Dorostkar, N.; Ghiaci, M.; Martinez-Huerta, M. V.; Fierro, J. L. G. "The Fabrication and Characterization of Cu-Nanoparticle Immobilization on a Hybrid Chitosan Derivative-Carbon Support as a Novel Electrochemical Sensor: Application for the Sensitive Enzymeless Oxidation of Glucose and Reduction of Hydrogen Peroxide", Journal of Materials chemistry B 2014, 2, pp. 706-717.

Tan, Y. W.; Gu, J. J.; Xu, W.; Chen, Z. P.; Liu, D. X.; Liu, Q. L.; Zhang, D. "Reduction of CuO Butterfly Wing Scales Generates Cu SERS Substrates for DNA Base Detection", ACS Applied Materials & Interfaces 2013, 5, pp. 9878-9882.

Muniz-Miranda, M.; Gellini, C.; Giorgetti, E. "Surface-Enhanced Raman Scattering from Copper Nanoparticles Obtained by Laser Ablation", The Journal of Physical Chemistry 2011, 115, pp. 5021-5027.

Im, H. G.; Jung, S. H.; Jin, J.; Lee, D.; Lee, J.; Lee, D.; Lee, J. Y.; Kim, I. D.; Bae, B. S. "Flexible Transparent Conducting Hybrid Film Using a Surface-Embedded Copper Nanowire Network: A Highly Oxidation-Resistant Copper Nanowire Electrode for Flexible Optoelectronics", ACS Nano 2014, 8, pp. 10973-10979.

Li, C. W.; Kanan, M. W. "CO2 Reduction at Low Overpotential on Cu Electrodes Resulting from the Reduction of Thick Cu2O Films", J. Am. Chem. Soc. 2012, 134, pp. 7231-7234.

Li, C. W.; Ciston, J.; Kanan, M. W. "Electroreduction of Carbon Monoxide to Liquid Fuel on Oxide-Derived Nanocrystalline Copper", Nature 2014, 508, pp. 504-507.

Marimuthu, A.; Zhang, J. W.; Linic, S. "Tuning Selectivity in Propylene Epoxidation by Plasmon Mediated Photo-Switching of Cu Oxidation State", Science 2013, 339, pp. 1590-1593.

McElwee-White, L. "Design of Precursors for the CVD of Inorganic Thin Films", Dalton Trans. 2006, pp. 5327-5333.

Lim, B. S.; Rahtu, A.; Gordon, R. G. "Atomic Layer Deposition of Transition Metals", Nature Materials 2003, 2, pp. 749-754.

Qiu, J. J.; Wei, W. D. "Surface Plasmon-Mediated Photothermal Chemistry", The Journal of Physical Chemistry 2014, 118, pp. 20735-20749.

Qiu, J. J.; Wu, Y. C.; Wang, Y. C.; Engelhard, M. H.; McElwee-White, L.; Wei, W. D. "Surface Plasmon Mediated Chemical Solution Deposition of Gold Nanoparticles on a Nanostructured Silver Surface at Room Temperature", Journal of the American Chemical Society 2013, 135, pp. 38-41.

Orendorff, C. J.; Gole, A.; Sau, T. K.; Murphy, C. J. "Surface-Enhanced Raman Spectroscopy of Self-Assembled Monolayers: Sandwich Architecture and Nanoparticle Shape Dependence", Analytical Chemistry 2005, 77, pp. 3261-3266.

Lippard, S. J.; Ucko, D. "Transition Metal Borohydride Complexes. II. Th Reaction of Copper(I) Compounds with Boron Hydride Anions", Inorganic Chemistry 1968, 7, pp. 1051-1056.

Gysling, H. J. "Coordination Complexes of Copper(I) Nitrate", Inorg. Synth. 1979, 19, pp. 92-97.

Zhang, X. Y.; Zhao, J.; Whitney, A. V.; Elam, J. W.; Van Duyne, R. P. "Ultrastable Substrates for Surface-Enhanced Raman Spectroscopy: Al2O3 Overlayers Fabricated by Atomic Layer Deposition Yield Improved Anthrax Biomarker Detection", J. Am. Chem. Soc. 2006, 128, pp. 10304-10309.

Richardson, H. H.; Carlson, M. T.; Tandler, P. J.; Hernandez, P.; Govorov, A. O. "Experimental and Theoretical Studies of Light-to-Heat Conversion and Collective Heating Effects in Metal Nanoparticle Solutions", Nano Lett. 2009, 9, pp. 1139-1146.

Baldwin, C. L.; Bigelow, N. W.; Masiello, D. J. "Thermal Signatures of Plasmonic Fano Interferences: Toward the Achievement of Nanolocalized Temperature Manipulation", The Journal of Physical Chemistry Letters 2014, 5, pp. 1347-1354.

Baffou, G.; Quidant, R. "Nanoplasmonics for Chemistry", Chem. Soc. Rev. 2014, 43, pp. 3898-3907.

Ye, W. C.; Chen, Y.; Zhou, F.; Wang, C. M.; Li, Y. M. "Fluoride-Assisted Galvanic Replacement Synthesis of Ag and Au Dendrites on Aluminum Foil with Enhanced SERS and Catalytic Activities", Journal of Materials Chemistry2012, 22, pp. 18327-18334.

Mcintyre, N. S.; Cook, M. G. "X-Ray Photoelectron Studies on Some Oxides and Hydroxides of Cobalt, Nickel, and Copper", Analytical Chemistry, 1975, 47, pp. 2208-2213.

Hernandez, J.; Wrschka, P.; Oehrlein, G. S. "Surface Chemistry Studies of Copper Chemical Mechanical Planarization", Journal of the Electrochemical Society 2001, 148, G389-G397.

DuChene, J. S.; Williams, B. P.; Johnston-Peck, A. C.; Qiu, J. J.; Gomes, M.; Amilhau, M.; Bejleri, D.; Weng, J. N.; Su, D.; Huo, F. W. et al. "Elucidating the Sole Contribution from Electromagnetic Near-Fields in Plasmon-Enhanced Cu2O Photocathodes", Advanced Energy Materials 2016, 6, pp. 1-10.

Nainan, K C.; E., R. G. "A New Synthesis of Amine- and Phosphine-Boranes", Inorganic Chemistry 1969, 8, pp. 2671-2674.

Gawande, M. B.; Goswami, A.; Felpin, F.-X.; Asefa, T.; Huang, X.; Silva, R.; Zou, X.; Zboril, R.; Varma, R. S. "Cu and Cu-Based Nanoparticles: Synthesis and Applications in Catalysis", Chemical Reviews 2016, 116, pp. 3722-3811.

Yang, Y.; Liu, J. Y.; Fu, Z. W.; Qin, D. "Galvanic Replacement-Free Deposition of Au on Ag for Core-Shell Nanocubes with Enhanced

(56) References Cited

OTHER PUBLICATIONS

Chemical Stability and SERS Activity", Journal of the American Chemical Society 2014, 136, pp. 8153-8156.

Madiyar, F. R.; Bhana, S.; Swisher, L. Z.; Culbertson, C. T.; Huang, X. H.; Li, J. "Integration of a Nanostructured Dielectrophoretic Device and a Surface-Enhanced Raman Probe for Highly Sensitive Rapid Bacteria Detection", Nanoscale 2015, 7, pp. 3726-3736.

Govorov, A. O.; Zhang, W.; Skeini, T.; Richardson, H.; Lee, J.; Kotov, N. A. "Gold Nanoparticle Ensembles as Heaters and Actuators: Melting and Collective Plasmon Resonances", Nanoscale Res. Lett. 2006, 1, pp. 84-90.

Williamson, M. J.; Tromp, R. M.; Vereecken, P. M.; Hull, R.; Ross, F. M. "Dynamic Microscopy of Nanoscale Cluster Growth at the Solid-Liquid Interface", Nature Materials 2003, 2, pp. 532-536.

Bocquet, F.; Maurel, C.; Roussel, J. M.; Abe, M.; Koudia, M.; Porte, L. "Segregation-Mediated Capping of Volmer-Weber Cu Islands Grown onto Ag(111)", Physical Review B 2005, 71, pp. 1-6.

Nilsing, M.; Persson, P.; Ojamae, L. "Anchor Group Influence on Molecule-Metal Oxide Interfaces: Periodic Hybrid DFT Study of Pyridine Bound to TiO2 via Carboxylic and Phosphonic Acid", Chemical Physics Letters 2005, 415, pp. 375-380.

Michota, A.; Bukowska, J. "Surface-Enhanced Raman Scattering (SERS) of 4-Mercaptobenzoic Acid on Silver and Gold Substrates", Journal of Raman Spectroscopy 2003, 34, pp. 21-25.

Wei, W.; Li, S. Z.; Qin, L. D.; Xue, C.; Millstone, J. E; Xu, X. Y.; Schatz, G. C.; Mirkin, C. A. "Surface Plasmon-Mediated Energy Transfer in Heterogap Au—Ag Nanowires", Nano Letters 2008, 8, pp. 3446-3449.

Aronoff, Y. G.; Chen, B.; Lu, G.; Seto, C.; Schwartz, J.; Bemasek, S. "Stabilization of Self-Assembled Monolayers of Carboxylic Acids on Native Oxides of Metals", Journal of the American Chemical Society 1997, 119, pp. 259-262.

Jiang, L.; You, T. T.; Yin, P. G.; Shang, Y.; Zhang, D. F.; Guo, L.; Yang, S. H. "Surface-Enhanced Raman Scattering Spectra of Adsorbates on Cu2O Nanospheres: Charge-Transfer and Electromagnetic Enhancement", Nanoscale 2013, 6, pp. 2784-2789.

Davidson, J. M., "Bis(triphenylphosphine)borohydridocopper(I)", Chemistry and Industry, 1964, 2021-2022.

* cited by examiner

SURFACE PLASMON-MEDIATED CHEMICAL DEPOSITION AND PLASMONIC STRUCTURES

CROSS-REFERENCE TO RELATED APPLICATION

This application is the 35 U.S.C. § 371 national stage application of PCT Application No. PCT/US2017/027927, filed Apr. 17, 2017, where the PCT claims the benefit of and priority to U.S. Provisional Application Ser. No. 62/324,400, having the title "SURFACE PLASMON-MEDIATED CHEMICAL DEPOSITION AND PLASMONIC STRUCTURES," filed on Apr. 19, 2016, the disclosures of which are incorporated herein by reference in theft entireties.

STATEMENT REGARDING FEDERALLY SPONSORED RESEARCH OR DEVELOPMENT

This invention was made with government support under DMR1352328 and CHE1038015 awarded by the National Science Foundation. The government has certain rights in the invention.

BACKGROUND

Copper nanoparticles (Cu NPs) have been of recent interest due to their earth-abundance, low cost, and potential use in various technological applications due to their optical characteristics, derived from a phenomenon known as surface plasmon resonance (SPR). These applications require high-purity nanostructured Cu films with clean surfaces (e.g., free of surfactants and/or adsorbed surface species) to perform the desired function. Thus, there is a need to produce appropriate materials.

SUMMARY

Embodiments of the present disclosure provide plasmonic structures, methods of making plasmonic structures, and the like. An embodiment of the present disclosure includes a method of forming a hybrid plasmonic structure, among others, that includes: a method of forming a hybrid plasmonic structure, comprising: exposing a plasmonic substrate to a precursor material; irradiating the plasmonic substrate and the precursor material with a light energy; and forming nanoparticles on the surface of the plasmonic substrate to form the hybrid plasmonic structure. In an embodiment, the nanoparticle is a metal nanoparticle, a polymer nanoparticle, or a bio-molecule nanoparticle. In an embodiment, the metal nanoparticle can have a diameter of about 1 to 20 nm. In an embodiment, the metal nanoparticle is selected from the group consisting of: a Cu nanoparticle, a Pt nanoparticle, a Pd nanoparticle, a Fe nanoparticle, a Ti nanoparticle, and a combination thereof, but is not a Au nanoparticle.

An embodiment of the present disclosure includes a composition, among others, that includes: a plasmonic structure including a plasmonic substrate having nanoparticles disposed on the surface of the plasmonic substrate. In an embodiment, the nanoparticle is a metal nanoparticle, a polymer nanoparticle, or a bio-molecule nanoparticle. In an embodiment, the metal nanoparticle is selected from the group consisting of: Cu, Pt, Pd, Fe, Ti, and a combination thereof. In an embodiment, the plasmonic substrate is selected from the group consisting of: AgFON, Ag nanobowl, CuFON, Cu nanobowl, Cu pyramid, AlFON, Al nanobowl, Al pyramid, and Ag pyramid.

Other compositions, methods, features, and advantages will be or become apparent to one with skill in the art upon examination of the following drawings and detailed description. It is intended that all such additional compositions, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 1A-C are images of SPMCSD of Cu NPs onto AgFON substrates at room temperature. SEM images of the AgFON substrate (FIG. 1A) before irradiation; (FIG. 1B) after visible-light irradiation ($\lambda$>435 nm) for 5 min at an incident power ($I_0$) of 2.0 W/cm$^2$ in the precursor solution; (FIG. 1C) after immersion in the precursor solution for 3 h under dark conditions.

(FIG. 3B) EDX spectrum of the AgFON substrate after deposition of the Cu NP film.

FIGS. 4A-B show surface enhanced Raman spectroscopy (SERS) spectra of the probe molecule 4-mercaptobenzoic acid (4-MBA) on the AgFON/Cu NP film substrate. (FIG. 4A) Diffuse-reflectance spectra of the AgFON substrate before (blue curve) and after (red curve) Cu NP film deposition; (FIG. 4B) Raman spectra of 4-MBA adsorbed on the nanostructured AgFON/Cu substrate (red line) from a 1 mM methanol solution. The spectrum obtained from the pure 4-MBA powder is shown for reference (black line).

FIGS. 5A-B are SEM images of the AgFON substrate. Ag film on nanosphere (AgFON) substrate includes a hexagonally close-packed silica nanosphere (d=310 nm) monolayer with a 150 nm Ag film on top.

FIG. 6 shows extinction spectrum of the AgFON substrate. To fully utilize this broad plasmonic response from the AgFON, a 300 W xenon lamp equipped with a 435 nm longpass filter was used to ensure sufficient optical excitation of the AgFON substrate while avoiding the direct absorption of light by the Cu precursor (see FIG. 8).

FIG. 7 shows TGA of $(Ph_3P)_2Cu(BH_4)$. From this experiment, the loss of mass ascribed to thermal decomposition of the solid was determined to begin at ca. 150° C.

FIG. 8 shows UV-Vis spectrum of $(Ph_3P)_2Cu(BH_4)$. A benzene solution of $(Ph_3P)_2Cu(BH_4)$ is colorless and shows no absorption in the visible range of the UV-Vis spectrum.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 25° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

General Discussion

Embodiments of the present disclosure provide plasmonic structures, methods of making plasmonic structures, and the like. Embodiments of the present disclosure can be used in catalysis, chemical and biological sensing, and nanofabrication for electronic devices. Previous techniques for formation of nanostructure on large-scale surfaces by traditional lithographic methods provides significant challenges. For example, chemical vapor deposition (CVD) of metal nanoparticles is limited by the thermal stability of precursors during vaporization and transport. In contrast, embodiments of the present disclosure use a "bottom-up" nanoscale approach, which allows the construction of materials from molecular or atomic components. Embodiments of the present disclosure can utilize the intrinsic surface properties to direct and control surface chemistry for nanostructure growth on substrate surfaces.

Plasmonic nanomaterials can include nanoscale metallic structures (e.g., Ag, Cu, and Al) that can efficiently convert low power light (e.g., sunlight) into heat due to their unique optical property called surface plasmon resonance (SPR). Embodiments of the present disclosure can include one of a number "bottom-up" approaches that can employ the SPR-generated photothermal heating to deposit nanoparticles (e.g., about 1 to 20 nm in diameter) or nanoparticle films at about room temperature, where intrinsic surface optical properties can be used to direct and control nanostructure growth. The surface plasmon mediated chemical solution deposition (SPMCSD) method allows the deposition to be conducted in the liquid phase at about room temperature or in the gas phase, offering mild operating conditions and low-energy consumption.

In an embodiment, a plasmonic structure can be produced using the bottom-up procedure described herein. An embodiment of the method can include exposing a plasmonic substrate to a precursor material in a vessel or appropriate chamber. The plasmonic substrate and the precursor material can be introduced to one another while the precursor material can be in the liquid phase (e.g., Example 1) or in the gas phase (e.g., gas phase Pd precursor compound). For example, in the liquid phase the precursor material is in liquid phase, while in the gas phase, the precursor material is a gas or vapor.

Subsequently, the plasmonic substrate and the precursor material can be irradiated with a light energy for a period of time. In an embodiment, the light energy is visible light and can have a power density of about 1.6 W/cm$^2$ to 2.8 W/cm$^2$. In an embodiment, the light energy can be provided by a Xenon light source, the sun, LED, laser, halogen lamp, or a combination thereof. In an embodiment, the exposure time of the plasmonic substrate and the precursor material to light energy can be about 1 to 5 minutes or more. In an embodiment, the exposure time and/or power density can be adjusted to a higher power and/or longer times to form a film on the plasmonic substrate. In an embodiment, the irradiation can be conducted at or near room temperature.

The plasmonic substrate converts the light energy into photothermal energy that generates local heating at the surface of the plasmonic substrate. In this regard, the light energy impinging upon the plasmonic substrate produces photothermally induced reactions on the surface of the plasmonic substrate so that nanoparticles (and nanoparticle films) are produced on the surfaced of the plasmonic substrate.

Upon exposure to the light energy, nanoparticles are formed on the surface of the plasmonic substrate to form a plasmonic structure. In an embodiment, the nanoparticles can have a diameter (or longest dimension) of about 1 to 100 nm, about 1 to 20 nm, about 2 to 10 nm, or about 2 to 5 nm. In an embodiment, the nanoparticles are spherical, non-spherical, polygonal, or the like. In an embodiment, the nanoparticles can cover about 10 to 100%, about 10 to 90%, about 20 to 90%, about 30 to 90%, about 40 to 90%, or about 50 to 90% of the surface of the plasmonic substrate. In an embodiment where the nanoparticles cover 100% of the surface, the nanoparticles form a nanoparticle film, where the film can have a thickness of about 20 to 250 nm, about 20 to 100 nm, about 20 to 70 nm, or about 50 to 60 nm.

In an embodiment, the nanoparticles can be metal nanoparticles, polymer nanoparticles, bio-molecule nanoparticles, oxides, or the like. In an embodiment, the metal nanoparticles can include Cu, Pt, Pd, Fe, Ti, nanoparticles, oxides of each (e.g., on the surface), or a combination thereof. In an embodiment, the metal nanoparticle is not gold. In an embodiment, the metal nanoparticles can have a diameter (or longest dimension) of about 1 to 20 nm, about 1 to 10 nm, or about 2 to 6 nm. In an embodiment, the polymer nanoparticle can be a polystyrene nanoparticle and other similar polymers. In an embodiment, the bio-molecule nanoparticle can be DNA nanoparticle, RNA nanoparticle, polynucleotide nanoparticle, polypeptide nanoparticle, or protein nanoparticle, as well as other similar bio-molecules. In an embodiment, the precursor material can be methyl (triphenylphosphine)gold(I), nitratobis(triphenylphosphine)copper(I), (cyclopentadienyl)(allyl)palladium(II), styrene, soybean oil, or the like. In an embodiment, the concentration of precursor material can be about 2 to 8 mg/mL or about 6 mg/mL.

In an embodiment, the plasmonic substrate can be a substrate that absorbs light energy and converts it to thermal energy. In an embodiment, the plasmonic substrate can be: AgFON, Ag nanobowls, CuFON, AlFON, Cu nanobowls, Al nanobowls, Cu pyramids, Al pyramids, or Ag pyramids. In an embodiment, the plasmonic substrate can have a diameter of about 50 nm to 1 µm.

As mentioned above, the plasmonic structure includes the plasmonic substrate having nanoparticles disposed on the surface of the plasmonic substrate. In an embodiment, the nanoparticle can be a metal nanoparticle or the nanoparticles can form a film on the surface of the plasmonic substrate. In an embodiment, the metal nanoparticle is selected to have moieties that are able to bond to organic compounds such as probes (e.g., Raman probe molecules). For example, the metal nanoparticle can include carboxylic acid moieties that can bond to the probe. In this way, the plasmonic structure can be used as a SERS platform. In an embodiment, the Raman probe molecules can include 4-aminobenzenthiol or 4-mercaptobenzoic acid.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

The photothermal heating of plasmonic metal nanostructures can be exploited for bottom-up nanofabrication via surface plasmon-mediated chemical solution deposition (SPMCSD). Herein, we demonstrate the versatility of this plasmon-mediated strategy with a rapid deposition (t 5 min) of metallic copper nanoparticles (Cu NPs) on a silver (Ag) film on nanosphere (AgFON) substrate under low power, visible-light irradiation ($I_0$=2.0 W/cm$^2$, λ>435 nm). The resultant plasmonic nanostructures exhibit significant optical extinction and enriched chemical affinity for Raman probe molecules, rendering the hybrid AgFON/Cu substrate a suitable plasmonic platform for chemical sensing via surface enhanced Raman scattering (SERS).

Copper nanoparticles (Cu NPs) have been of recent interest due to their earth-abundance, low cost, and potential use in various technological applications.[1-3] Specifically, their extraordinary optical characteristics, derived from a phenomenon known as surface plasmon resonance (SPR),[4-7] have been widely used in chemical sensing,[2,8-10] optoelectronics,[11] and catalysis.[1,3,12-14] These applications require high-purity nanostructured Cu films with clean surfaces (e.g., free of surfactants and/or adsorbed surface species) to perform the desired function. Although several chemical processes have been developed to achieve conformal Cu films (e.g., chemical vapor deposition or atomic layer deposition), these methods require high substrate temperatures and are limited by constraints on the physical properties and decomposition chemistry of precursor molecules.[15,16]

We recently developed a technique known as surface plasmon-mediated chemical solution deposition (SPMCSD) for nanomaterials synthesis via "bottom-up" assembly from molecular precursors.[17,18] It was demonstrated that SPR excitation of a nanostructured Ag substrate initiated the decomposition of CH$_3$AuPPh$_3$ molecules in solution via plasmon-driven photothermal heating to mediate the deposition of sub-15 nm Au NPs at room temperature.[18] A lower limit for the AgFON substrate temperature under SPMCSD conditions was obtained by photothermal polymerization of soybean oil (T≥230° C.) under visible-light irradiation (λ>515 nm) using a low-power xenon lamp.[18] The SPR-driven localized heating of the plasmonic Ag substrate enabled a self-limited photochemical deposition process that could be tuned by varying the amount of time the reaction was allowed to proceed.[18] Significantly, the Au NPs deposited via SPMCSD are free of surface ligands, yielding a clean surface requisite for a variety of applications in catalysis and sensing. In principle, this SPMCSD strategy should be suitable for constructing various materials to build hybrid plasmonic substrates.[17]

Here, we showcase the versatility of the SPMCSD method with the demonstration of Cu NP deposition by exploiting the localized photothermal heating of a Ag film on nanosphere (AgFON) substrate to thermally decompose the Cu precursor tetrahydroboratobis(triphenylphosphine)copper(I) [(Ph$_3$P)$_2$Cu(BH$_4$)] in benzene solution at room temperature. Metallic Cu NPs were rapidly (t~5 min) formed on the AgFON substrate upon low power ($I_0$=2.0 W/cm$^2$) visible-light irradiation ($\lambda$>435 nm). Interestingly, the photothermal deposition was so efficient that the AgFON substrate was completely coated with a rough Cu film within 5 minutes by simply increasing the incident power density (A) to 2.8 W/cm$^2$. Compared with traditional vapor phase deposition, this method offers mild operating conditions and low energy consumption while rapidly furnishing a plasmonic platform free of surface-adsorbed species.

Experimental Section

Chemicals.

A suspension of silica beads (0.31 μm in diameter, 9.83 wt. % in water) was purchased from Bangs Laboratories, Inc. and stored at 4° C. until use. Silicon (111) was purchased from Cemat Silicon S.A. Triphenylphosphine was purchased from Acros. Copper(II) nitrate trihydrate [Cu(NO$_3$)$_2$·3H$_2$O], methanol, dichloromethane, and 4-mercaptobenzoic acid (4-MBA) were purchased from Sigma Aldrich. Sodium borohydride (NaBH$_4$), diethyl ether, and hexanes were purchased from Fisher Scientific. Absolute ethanol was purchased from Decon Laboratories. Nitratobis(triphenylphosphine)copper(I) was synthesized as described previously.[19] Benzene was purified with an MBraun MB-SP solvent purification system and stored over 3 A molecular sieves prior to use. All other reagents were used as received without further purification. Unless otherwise specified, all synthetic procedures were performed under an inert atmosphere (N$_2$, Ar) using standard Schlenk line and glovebox techniques.

Characterizations.

$^1$H and $^{31}$P NMR spectra were obtained using Mercury 300 MHz spectrometers and referenced to the residual protons of the deuterated solvents. Thermogravimetric analyses (TGA) were performed on a TA instruments Q5000. The sample was heated from 22° C. to 500° C. under N$_2$ atmosphere at a heating rate of 10° C./min. Infrared spectroscopy was performed on a Perkin Elmer Spectrum One FT-IR spectrometer using a universal ATR sampling accessory. After each deposition, the substrate was characterized by scanning electron microscopy (SEM, FEI SEM), energy dispersive X-ray spectroscopy (EDX, GENESIS) and X-ray photoelectron spectroscopy (XPS, PHI 5000 VersaProbe II). SEM experiments were conducted with 15 kV accelerating voltage. In XPS experiments, the system used a focused monochromatic Al Kα X-ray (1486.6 eV) excitation source and a spherical section analyzer. Adventitious carbon (284.8 eV) was used as a binding energy reference to correct for specimen charging effect. A 50 W X-ray beam was focused to a 200 μm diameter area on the sample. The X-ray beam is incident normal to the sample and the photoelectron detector is at 45° off-normal.

Synthesis of Tetrahydroboratobis(triphenylphosphine)copper(I) [(Ph$_3$P)$_2$Cu(BH$_4$)]

The synthesis was adapted from previously reported procedures.[20,21] Briefly, NaBH$_4$ (89.0 mg, 2.35 mmol) was dissolved in 10 mL absolute ethanol. In a separate flask, Nitratobis(triphenylphosphine)copper(I) (1.30 g, 2.01 mmol) was dissolved in 20 mL dichloromethane. The ethanol solution was then added to the dichloromethane solution and stirred for 30 minutes. This solution was then filtered and washed with 4 mL of dichloromethane followed by 8 mL hexanes. The filtrate was allowed to stand at −20° C. for several hours to produce crystals. This crude product was collected and recrystallized from 8 mL dichloromethane and 2 mL hexanes at −20° C. The solid was then filtered and dried under vacuum to afford the product as a white microcrystalline solid in 56% yield. $^1$H NMR (300 MHz, C$_6$D$_6$) δ 6.93 (m, 18H), 7.47 (m, 12H). $^{31}$P NMR (121 MHz, C$_6$D$_6$) δ-1.19 (broad). IR (neat) 1140, 1936, 1989, 2265, 2378, 2399 cm$^{-1}$. The spectroscopic data were comparable to previously reported values.[20]

AgFON Substrate Preparation.

A 1 cm$^2$ Si wafer was washed with sonication in a mixed solution of deionized water, acetone, and ethanol (1:1:1 by volume) and then O$_2$ plasma-cleaned for 3 min. The silica-nanosphere suspension was diluted in a solution of ethanol and water (1:4 by volume) and then drop-cast onto the pretreated Si wafer. After evaporation of the solvent overnight, a 150 nm Ag film was deposited through physical sputtering (KJL CMS-18 Multi-Source) on the nanosphere-covered substrate. The extinction spectra were collected on a UV-Vis spectrophotometer (Shimadzu, UV 2600).

Chemical Deposition of Cu Nanoparticle Films.

Precursor solutions were made by dissolving 6 mg of (Ph$_3$P)$_2$Cu(BH$_4$) in 2 mL of benzene in a glovebox. The AgFON substrate was cleaned with N$_2$ gas before immersion in 1.5 mL of precursor solution within a tubular Schlenk flask. The substrate was then irradiated for a given period of time (typically 5 min) with visible light ($\lambda$>435 nm) from a xenon lamp (2.0 W/cm$^2$). After deposition, the substrate was washed several times with copious amounts of pure benzene and finally dried under a stream of N$_2$ gas.

Results and Discussion

Figure 1A:
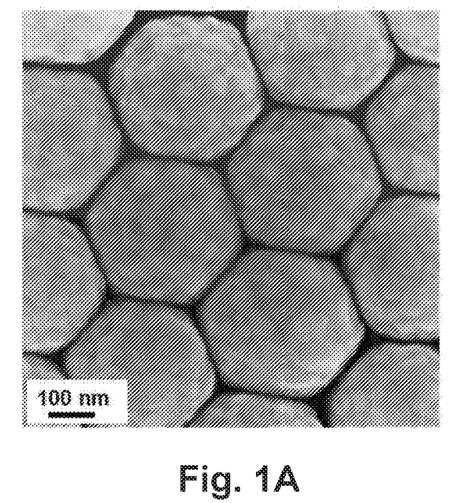
Figure 5A:
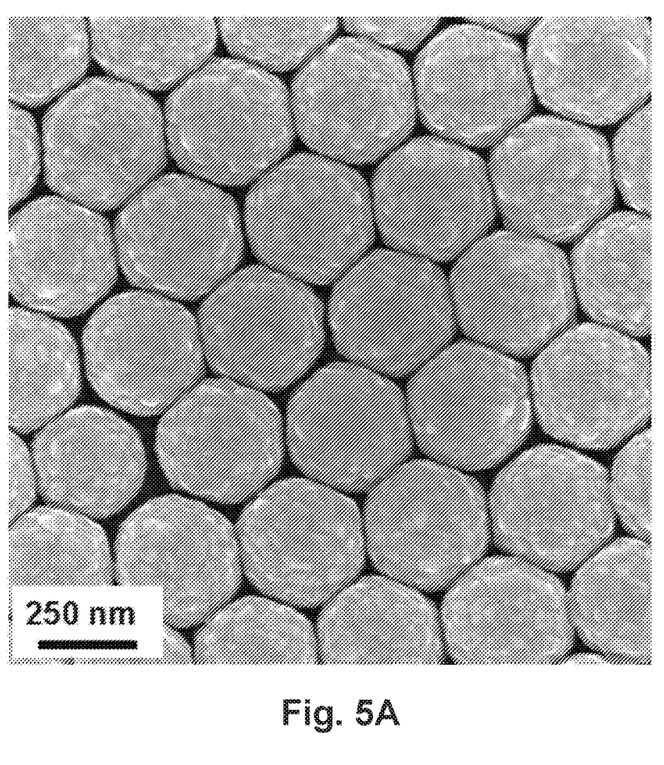
FIG. 5A shows a low-magnification SEM image of the AgFON substrate, illustrating the excellent long-range order and uniformity of the close-packed nanosphere pattern.
Figure 5B:
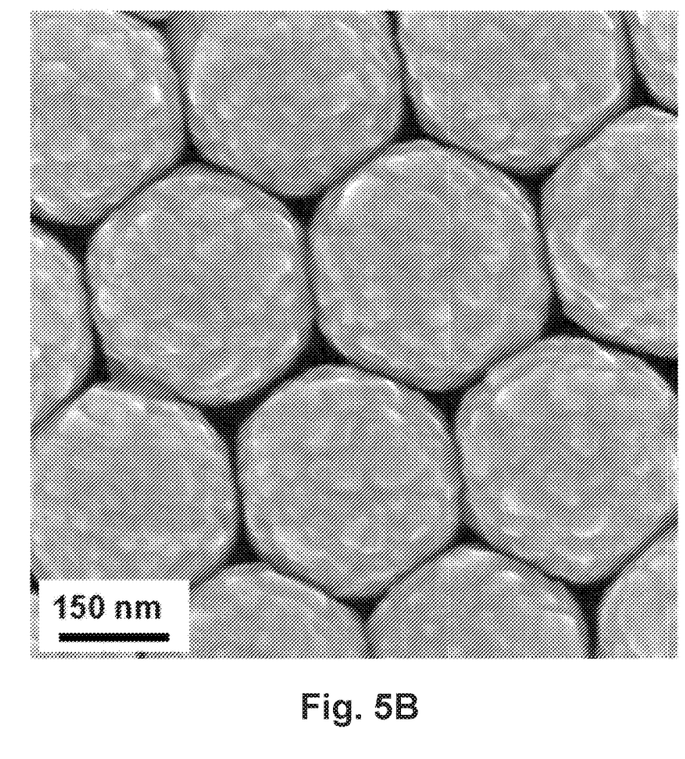
FIG. 5B is a high-magnification SEM image of the same AgFON substrate showing the surface roughness of the Ag film.
Figure 6:
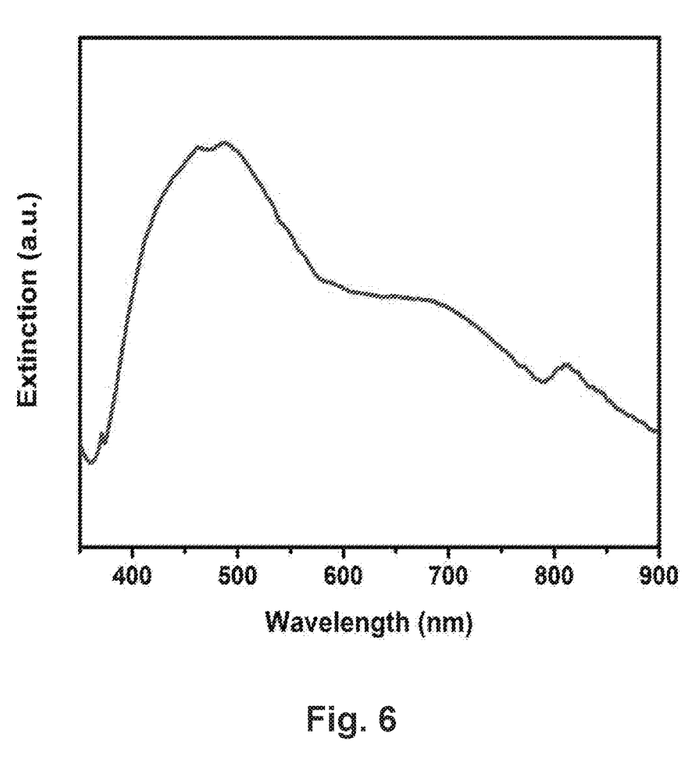

Fabrication of the plasmonic AgFON substrate has been described elsewhere[18] and experimental details are contained in the Experimental Section. Briefly, SiO$_2$ NPs (~310 nm in diameter) were self-assembled on a Si wafer to form a hexagonally close-packed monolayer. A 150 nm thick Ag film was subsequently sputtered onto the self-assembled SiO$_2$ platform to form the AgFON substrate, as shown in FIG. 1A and FIGS. 5A-B. The as-fabricated AgFON substrate exhibits a distinctive SPR feature in the visible range of the spectrum (FIG. 6) that is consistent with a previous report.[22] This AgFON substrate therefore serves as a plasmonic platform for the photothermal decomposition of organometallic Cu precursors.

Figure 7:
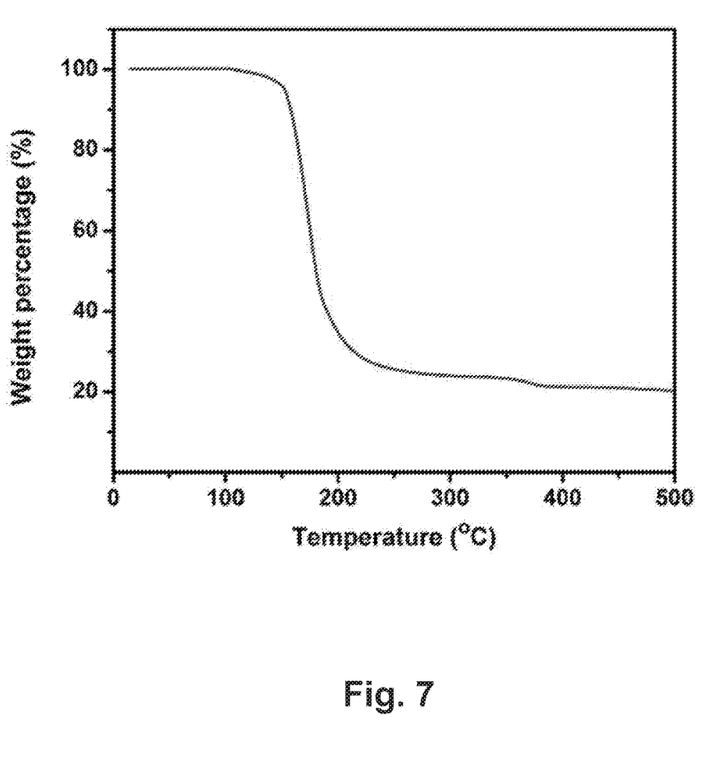
Figure 8:
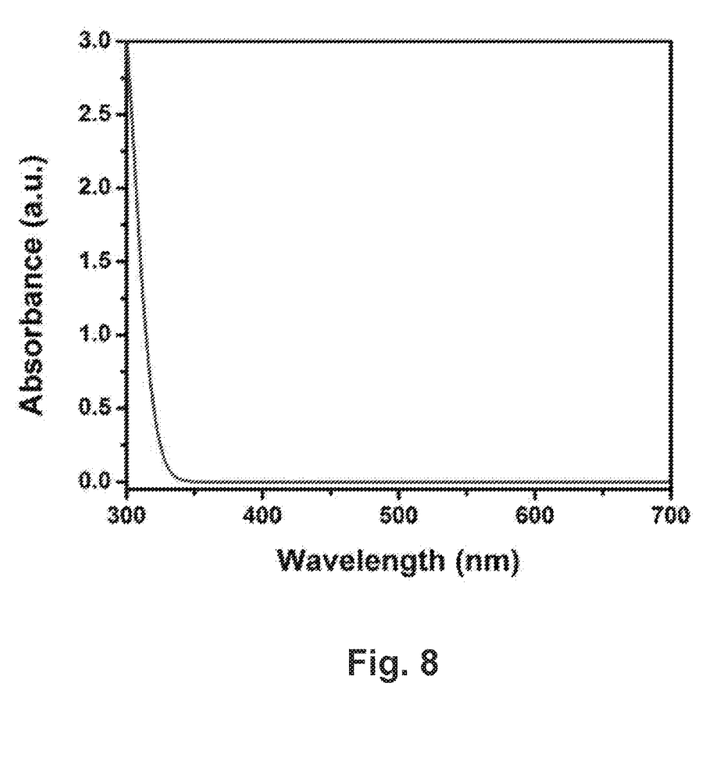

Surface plasmon excitation of the AgFON substrate induces rapid photothermal heating via nonradiative damping of SPR.[23,24] Swift heat exchange at the nanoscale ensures that thermal equilibrium is rapidly reached within several nanoseconds.[25] Our previous studies have shown that the surface temperature of the AgFON substrate quickly rises to an elevated value (T≥230° C.) that is then maintained throughout the duration of the photothermal reaction.[18] Thermogravimetric analysis (TGA) of (Ph$_3$P)$_2$Cu(BH$_4$) shows that in the solid state, the Cu precursor decomposes between 150° C. and 200° C. (FIG. 7). The TGA provides an upper limit for the onset of thermal decomposition and, indeed, the solution decomposition temperature has been reported to be significantly lower.[26] Because $(Ph_3P)_2Cu(BH_4)$ lacks any optical absorption in the visible region of the spectrum (FIG. 8), visible-light irradiation should selectively excite the SPR of the AgFON substrate without direct optical excitation of the Cu precursor. Having previously deposited Au NPs on AgFON substrates from a gold precursor ($CH_3AuPPh_3$) with a solid phase decomposition temperature of 150° C. via SPMCSD,[18] resonant optical excitation is expected to generate sufficient surface heating to drive deposition of Cu NPs from $(Ph_3P)_2Cu(BH_4)$ molecules.

Figure 1B:
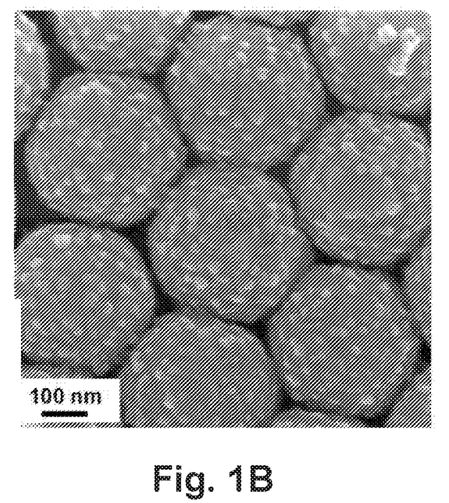
Figure 1C:
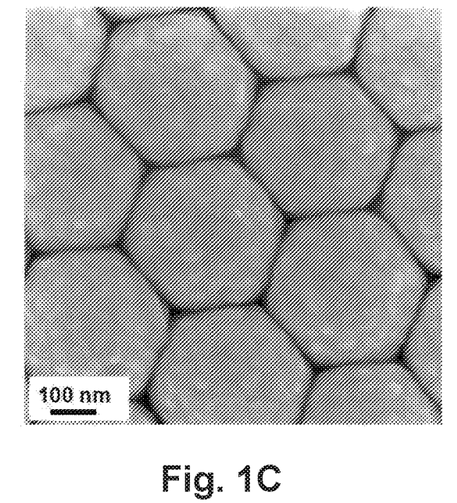

In a typical experiment, a AgFON substrate was immersed into a benzene solution containing $(Ph_3P)_2Cu(BH_4)$ at room temperature and irradiated with visible light ($\lambda>435$ nm) for 5 minutes using a xenon lamp ($I_0=2.0$ W/cm$^2$). The bulk solution temperature was monitored via a thermocouple throughout the duration of the SPMCSD reaction and was observed to reach ca. 40° C. Inspection of the substrate with scanning electron microscopy (SEM) after irradiation shows an obvious change in surface roughness on the Ag surface with the occurrence of many NPs on the AgFON substrate (FIG. 1B). No change in substrate morphology or appearance of NPs was observed when a control experiment was conducted under dark conditions for 3 h, confirming that light irradiation is required to initiate NP deposition (FIG. 1C).

Figure 2A:
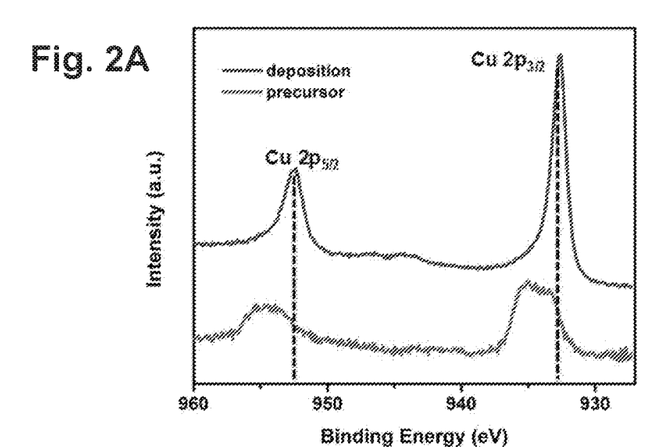
FIGS. 2A-D provide XPS analysis of the as-deposited NP films on AgFON substrates (blue curves) and the precursor $(Ph_3P)_2Cu(BH_4)$ molecules (red curves) for comparison. Detailed elemental scans of (FIG. 2A) Copper (Cu) 2p region, (FIG. 2B) Cu LMM Auger region, (FIG. 2C) Phosphorus (P) 2p region, and (FIG. 2D) Boron (B) is region.
Figure 2B:
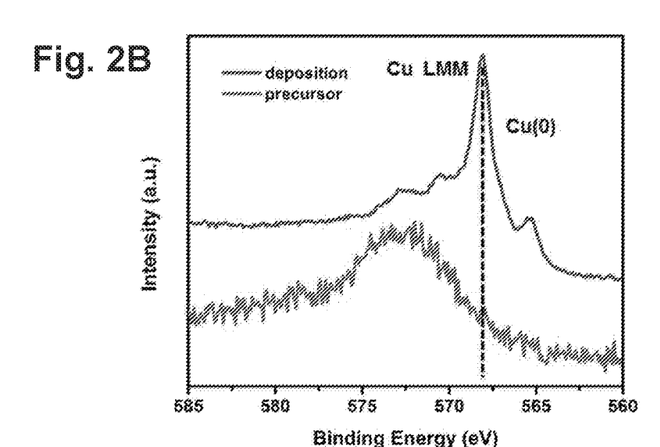
Figure 9:
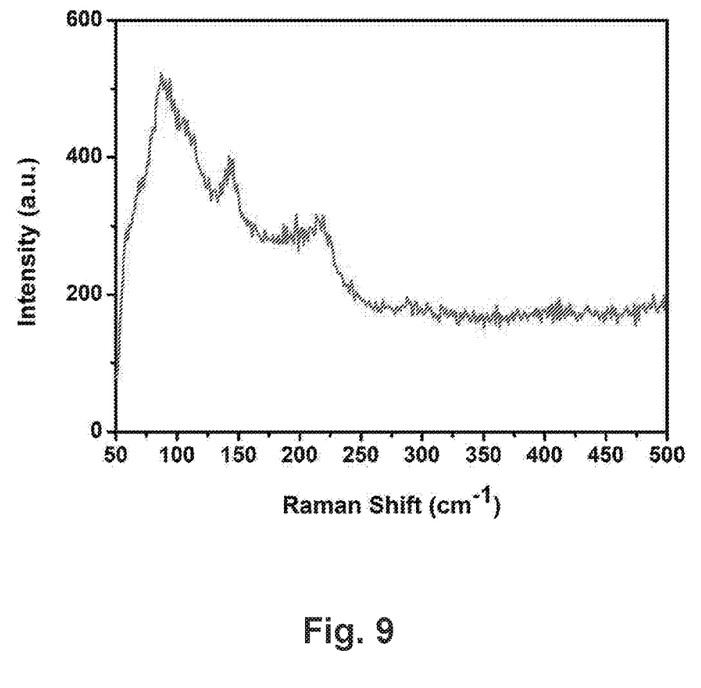
FIG. 9 shows Raman spectrum of the AgFON substrate after 5-minute deposition of Cu nanoparticle film. Raman spectroscopy was used to identify the surface species on the AgFON substrate after Cu nanoparticle film deposition. The spectrum was collected using a Horiba confocal Raman spectrometer with a 532 nm laser as the excitation source. The Raman features observed are indicative of the presence of $Cu_2O$, suggesting that the Cu surface underwent partial oxidation upon exposure to ambient air during sample transfer.

Several methods were then employed to characterize the as-deposited NPs. The chemical state of Cu was investigated with X-ray photoelectron spectroscopy (XPS). Comparison of the binding energies from the Cu 2p and Cu LMM regions of the Cu precursor (before reaction) and the Cu NPs (after reaction) confirms a change in chemical state during the SPMCSD process (FIGS. 2A and 2B). Additionally, the spectrum of the Cu NPs exhibits two peaks with binding energies of 932.6 eV and 952.5 eV in the Cu $2p_{3/2}$ and Cu $2p_{1/2}$ regions, respectively (FIG. 2A). The satellite peak characteristic of Cu(II) at ca. 943 eV was absent in the detailed element scan (FIG. 2A), excluding the possibility that the deposited NPs are CuO.[27] As the binding energies of Cu(0) and Cu(I) are very similar in the Cu $2p_{3/2}$ region, the Cu LMM Auger electron region was used to distinguish between these oxidation states (FIG. 2B). The dominant peak at 568.0 eV clearly shows that the major component of the deposited NPs is made of metallic Cu(0).[28] The slight shoulder at 569.8 eV indicates the presence of Cu(I) from a thin layer of $Cu_2O$ on the metallic Cu NP surface, which likely forms during sample transfer. Raman spectroscopy of the substrate confirms the presence of a thin layer of $Cu_2O$ (FIG. 9),[29] consistent with the XPS results (FIGS. 2A and 2B). Since the substrate itself does not induce the decomposition of $(Ph_3P)_2Cu(BH_4)$ in the dark (FIG. 1C), and the precursor has no absorption in the irradiation range used for the reaction (FIG. 8), these results are consistent with photothermal decomposition of Cu precursors to yield Cu NPs via SPR excitation of the underlying AgFON substrate.

The thermal decomposition of $(Ph_3P)_2Cu(BH_4)$ in benzene solution occurs at temperatures as low as 50° C. and has been reported to evolve hydrogen gas ($H_2$), triphenylphosphine ($Ph_3P$), and borane triphenylphosphine ($PPh_3.BH_3$), as shown in the following reaction:[26]

$$(Ph_3P)_2Cu(BH_4) \xrightarrow{\Delta} Cu + \frac{1}{2}H_2 + Ph_3P + Ph_3P \bullet BH_3 \quad (1)$$

Figure 2C:
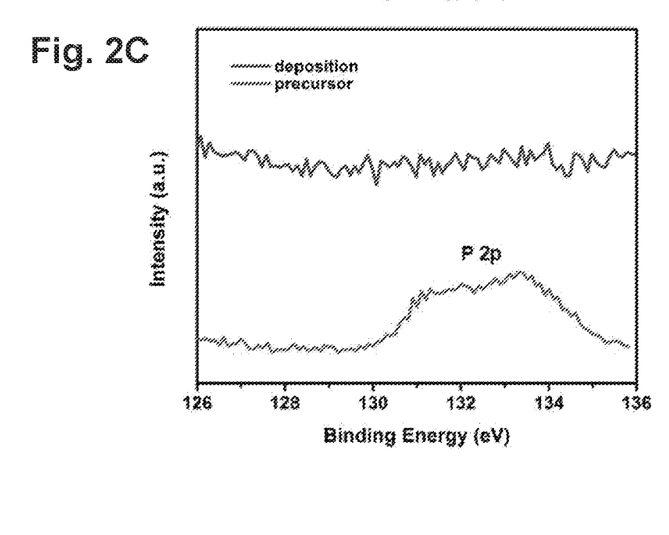
Figure 2D:
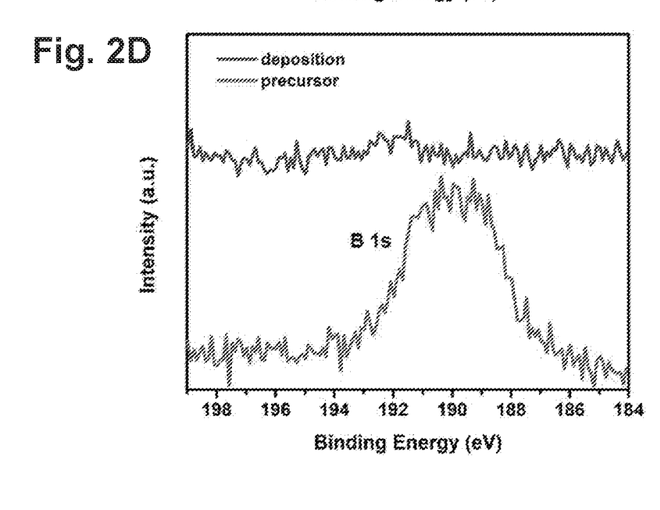

Therefore, a complete decomposition of the Cu precursor is expected at the elevated surface temperatures (T≥230° C.) achieved under our experimental conditions.[18] Because the $Ph_3P$ and $Ph_3P.BH_3$ byproducts are highly soluble in benzene[30] and the $H_2$ gas will reside in the reactor headspace, the SPMCSD reaction should yield ligand-free Cu NPs in high purity. As anticipated, XPS analysis of the substrate after Cu NP deposition confirms that there are no residual ligands associated with the substrate after reaction (FIGS. 2C and 2D). This SPMCSD approach thereby provides high-purity Cu NPs on the AgFON substrate that could serve as a plasmonic platform for a variety of applications in catalysis[31] and chemical sensing.[32,33]

Figure 3A:
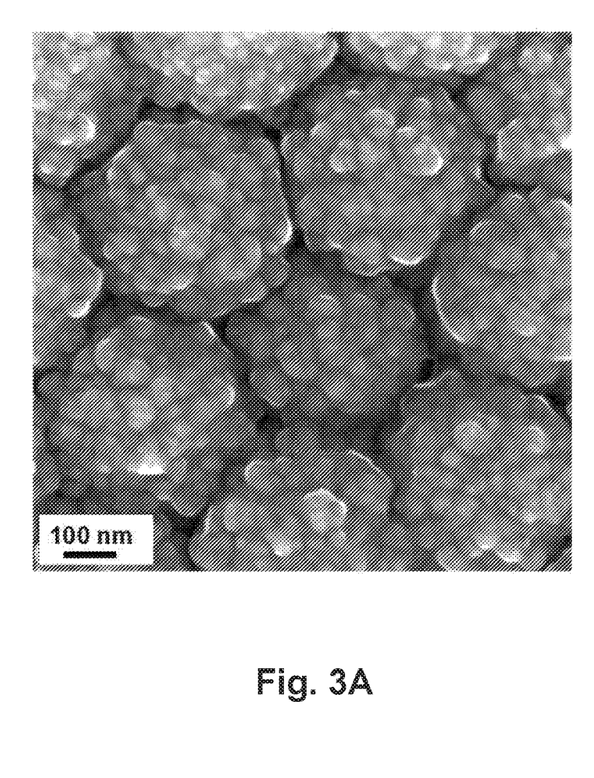
FIGS. 3A-B are images of SPMCSD of Cu NP films onto AgFON substrates at room temperature. SEM images of the AgFON substrate (FIG. 3A) after visible-light irradiation for 5 min under increased incident power ($I_0$=2.8 W/cm$^2$)
Figure 3B:
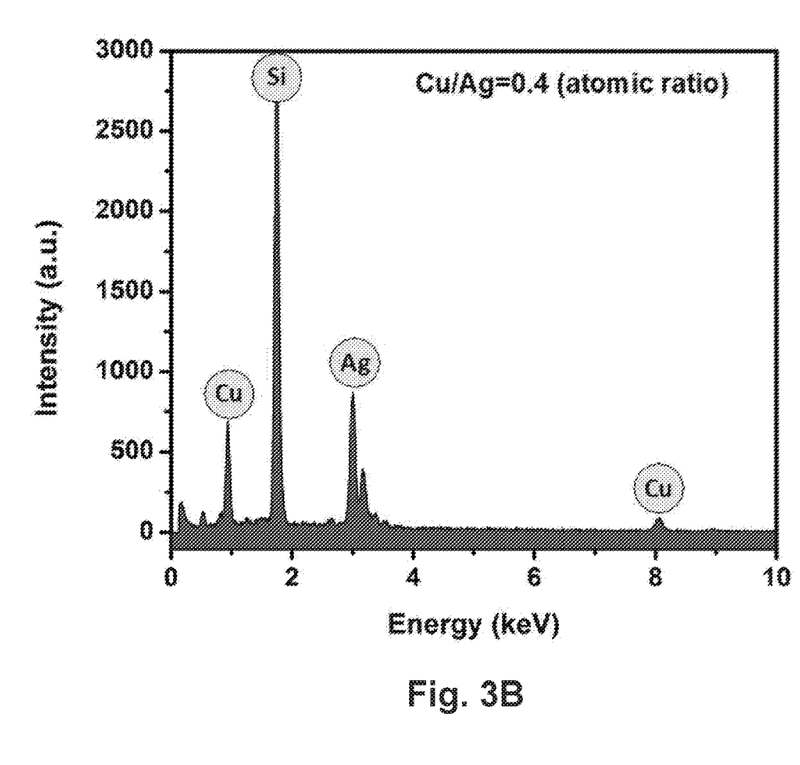
Figure 10A:
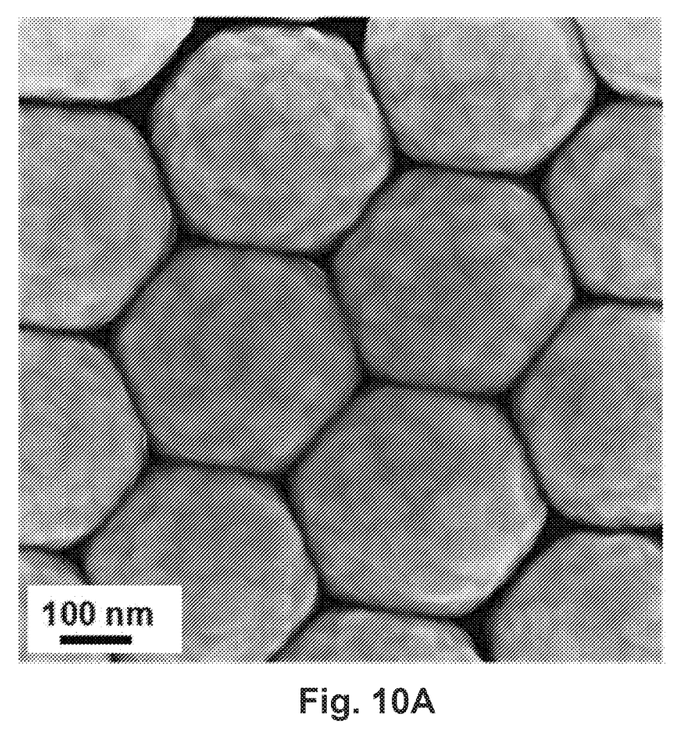
FIGS. 10A-B are SEM images of the AgFON substrate (FIG. 10A) before irradiation and (FIG. 10B) after visible-light irradiation for 30 minutes under 2.0 $W/cm^2$. To investigate the role of deposition time in the SPMCSD process, the AgFON substrate was immersed in a fresh precursor solution (same amount and concentration) and irradiated for 30 minutes instead of the standard 5-minute reaction.
Figure 10B:
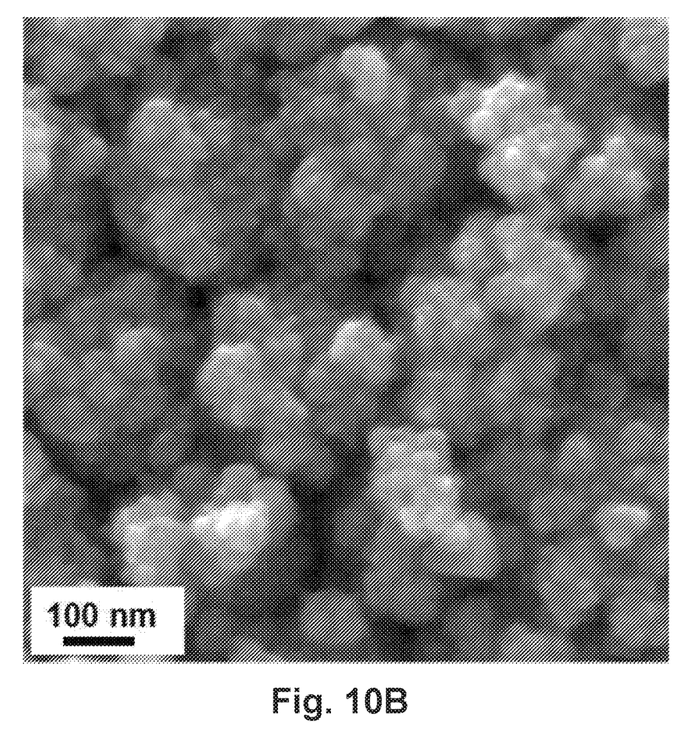

In addition to the deposition of Cu NPs, a conformal Cu NP film was easily achieved by simply adjusting either the incident power density or the total irradiation time. Previous theoretical work shows that the plasmonic heating efficiency is proportional to the excitation power density,[34] and therefore higher power irradiation was expected to induce faster reaction rates. Indeed, a Cu NP film was rapidly achieved within 5 minutes when the SPMCSD was conducted under increased incident power density ($I_0=2.8$ W/cm$^2$) (FIG. 3A). Analysis of the film composition by energy dispersive X-ray spectroscopy shows signals of both Ag and Cu with a Cu:Ag atomic ratio of 0.4 (FIG. 3B). Using the thickness of the sputtered Ag film as an internal reference (150 nm), the deposited Cu film was estimated to be ca. 60 nm thick. Alternatively, a metallic Cu film could also be obtained under relatively lower power ($I_0=2.0$ W/cm$^2$) if the reaction was allowed to proceed for a longer period of time (30 min instead of 5 min) (FIG. 10A-B). Based on these observations, it appears that Cu atoms nucleate to form NPs in the initial stages of precursor decomposition and then eventually coalesce into a continuous NP-based film. Such Cu thin-film growth behavior agrees well with the 222109_8280Volmer-Weber model of film deposition.[35] It is noted that a similar Volmer-Weber growth mode was observed for the growth of Cu islands on a Ag surface under ultrahigh vacuum (UHV) conditions.[36]

Figure 4A:
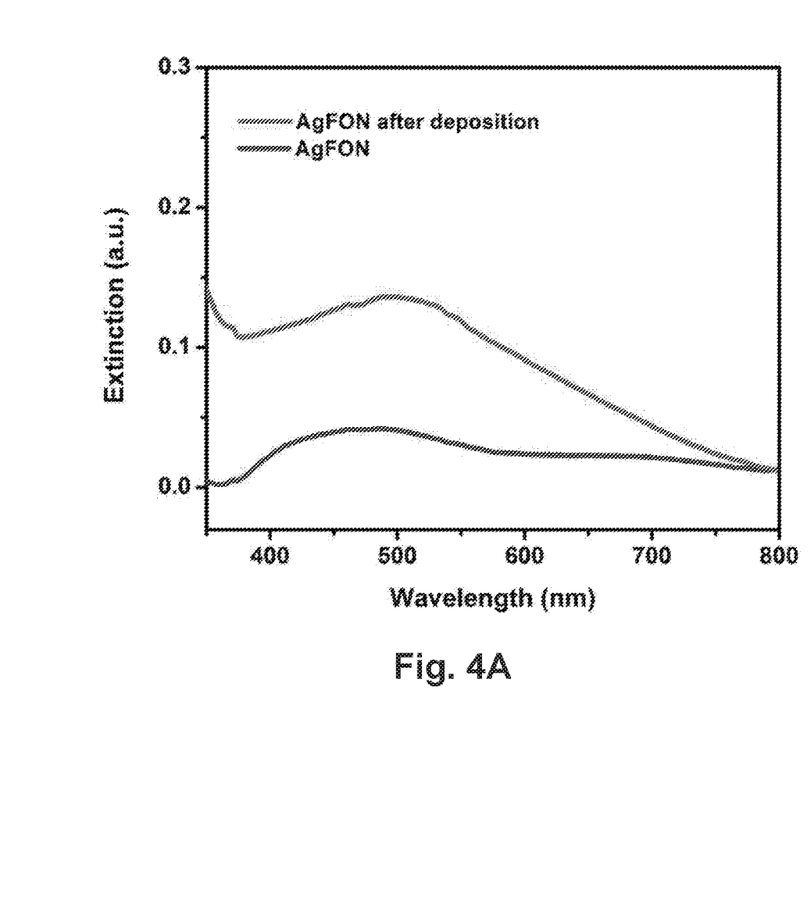
Figure 4B:
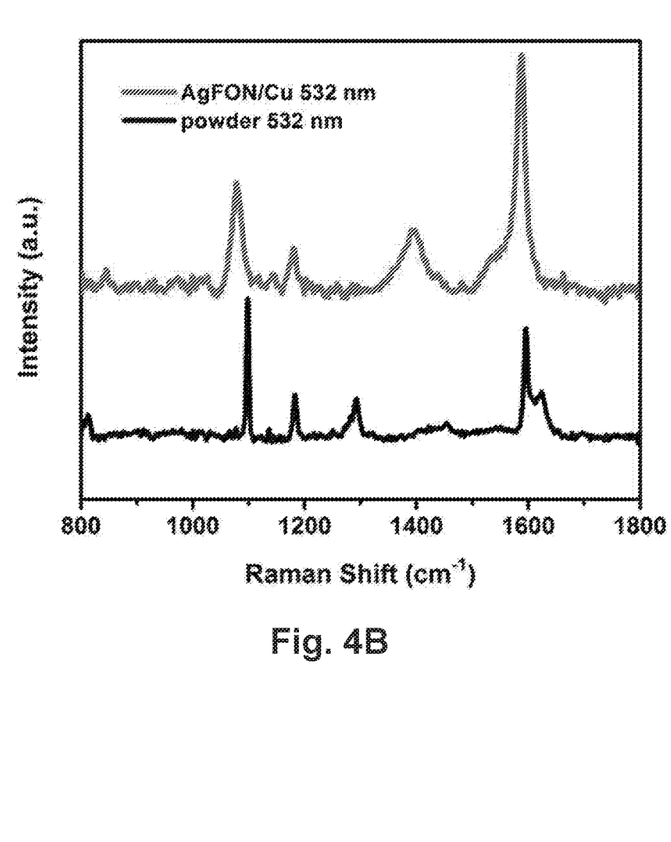
Figure 11A:
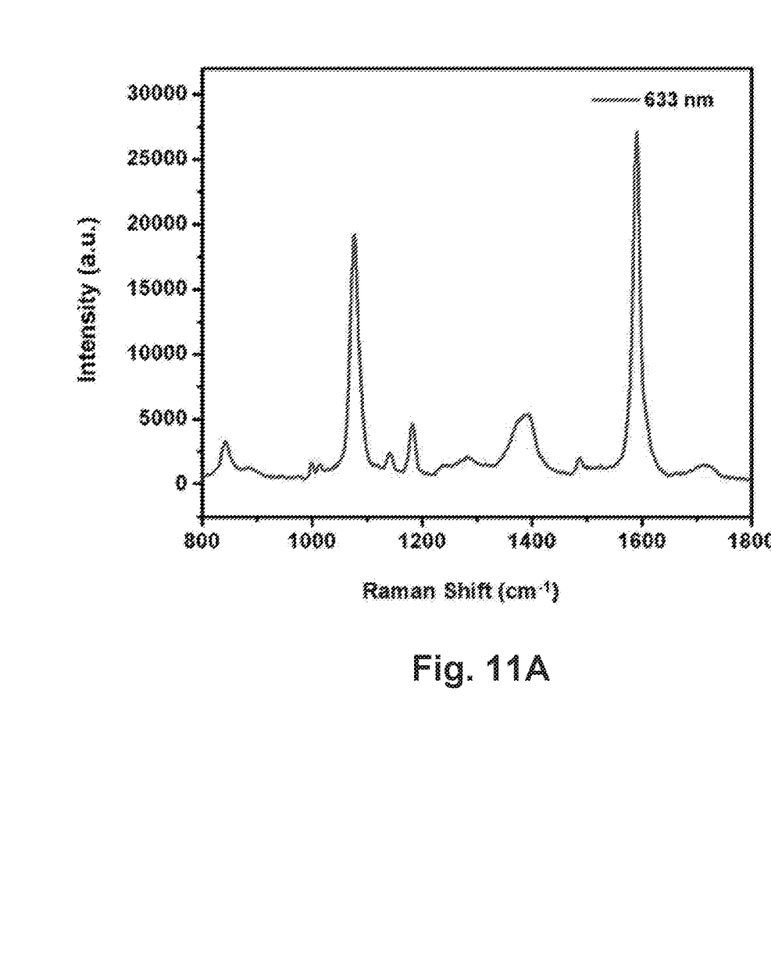
FIGS. 11A-B show the SERS measurements of the same substrate using 633 nm and 785 nm lasers, respectively. The number of gratings in the Raman spectrometer was 600 grooves/mm. The irradiation power was 0.6 mW and the acquisition time was 10 s for 2 cycles.
Figure 11B:
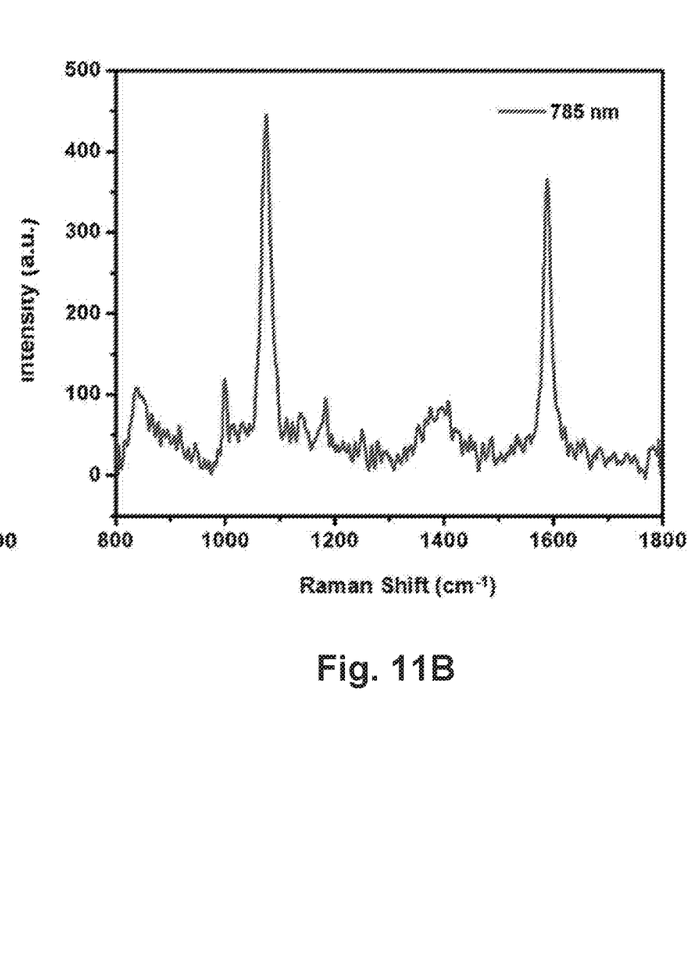

Compared to the initial AgFON substrate, the newly formed AgFON/Cu NP film substrate (FIG. 3A) exhibits significant extinction across the entire visible spectrum (400-700 nm) with a peak maximum ($\lambda_{max}$) at ca. 500 nm (FIG. 4A), making the hybrid plasmonic substrate an intriguing platform for surface enhanced Raman scattering (SERS) applications. Moreover, the native oxide (i.e. $Cu_2O$) on the Cu surface offers unique opportunities to interact with Raman-active molecules containing carboxylic acid moieties that would otherwise not adsorb to Au or Ag-based SERS substrates.[37] The Raman probe molecule 4-mercaptobenzoic acid (4-MBA) was chosen to illustrate the advantages of a AgFON/Cu substrate as a plasmonic SERS platform. FIG. 4B shows the SERS spectra of 4-MBA adsorbed onto the AgFON/Cu substrate (red line) along with the pure 4-MBA powder itself for reference (black line) collected under 532 nm laser excitation. The dominant features located at ca. 1084 cm$^{-1}$ and 1586 cm$^{-1}$ were assigned to $v_{8a}$ ($a_1$) and $v_{12}$ ($a_1$) aromatic ring vibrations, respectively, while the signal at ca. 1182 cm$^{-1}$ ($v_9$, $a_1$) arises from the C—H deformation mode.[38,39] It is noted that the COO$^-$ vibrational mode observed at ca. 1290 cm$^{-1}$ in the pure 4-MBA powder shifted to ca. 1390 cm$^{-1}$ upon adsorption on the $Cu_2O$ surface. Such a significant shift in this vibrational mode confirms that the carboxylate groups preferentially anchor the Raman probe molecules to the native oxide on the AgFON/Cu surface.[40,41] From these experiments, the magnitude of the SERS enhancement factor (EF)

from the AgFON/Cu hybrid structure was estimated to be on the order of ~$10^5$. It should be noted that this SERS EF is obtained solely from the Cu portion of the substrate, as the thickness of the Cu film (~60 nm) prevents any near-field enhancement originating from the underlying AgFON substrate. SERS experiments were also conducted using 633 nm and 785 nm laser excitation to correlate the SERS EF with the plasmonic response of the hybrid substrate. As expected, the largest SERS EF was observed under 532 nm, while very minimal SERS enhancements were observed under 785 nm laser excitation (FIGS. 11A-B).

CONCLUSION

In summary, we have successfully demonstrated the deposition of high-purity Cu NP films by SPMCSD at room temperature from solution-phase precursors. This hybrid AgFON/Cu plasmonic platform was further shown to exhibit unique surface affinity for SERS probe molecules (4-MBA) and significant SERS EFs of ~$10^5$ under resonant optical excitation (532 nm). Taken together, these studies demonstrate the remarkable capability of the SPMCSD process for exploiting the intrinsic surface and optical properties of plasmonic nanomaterials to direct and control nanostructure growth. It is anticipated that this SPMCSD strategy should be amenable to the deposition of a variety of earth-abundant materials from different phases (both liquid- and gas-phase) at or near room temperature for the continued development of various technological applications that require clean surfaces with nanostructured features (e.g. catalysis and chemical sensing).

Example 1 References (1) Du, J. L.; Chen, Z. F.; Ye, S. R.; Wiley, B. J.; Meyer, T. J. Copper as a Robust and Transparent Electrocatalyst for Water Oxidation. *Angew. Chem. Int. Ed.* 2015, 54, 2073-2078.
(2) Kowalska, A. A.; Kaminska, A.; Adamkiewicz, W.; Witkowska, E.; Tkacz, M. Novel Highly Sensitive Cu-Based SERS Platforms for Biosensing Applications. *J. Raman Spectrosc.* 2015, 46, 428-433.
(3) Zhao, J.; Tran, P. D.; Chen, Y.; Loo, J. S. C.; Barber, J.; Xu, Z. J. Achieving High Electrocatalytic Efficiency on Copper: A Low-Cost Alternative to Platinum for Hydrogen Generation in Water. *ACS Catal.* 2015, 5, 4115-4120.
(4) Chan, G. H.; Zhao, J.; Hicks, E. M.; Schatz, G. C.; Van Duyne, R. P. Plasmonic Properties of Copper Nanoparticles Fabricated by Nanosphere Lithography. *Nano Lett.* 2007, 7, 1947-1952.
(5) Duan, J. L.; Cornelius, T. W.; Liu, J.; Karim, S.; Yao, H. J.; Picht, O.; Rauber, M.; Muller, S.; Neumann, R. Surface Plasmon Resonances of Cu Nanowire Arrays. *J. Phys. Chem. C* 2009, 113, 13583-13587.
(6) Susman, M. D.; Feldman, Y.; Vaskevich, A.; Rubinstein, I. Chemical Deposition and Stabilization of Plasmonic Copper Nanoparticle Films on Transparent Substrates. *Chem. Mater.* 2012, 24, 2501-2508.
(7) Lu, S. C.; Hsiao, M. C.; Yorulmaz, M.; Wang, L. Y.; Yang, P. Y.; Link, S.; Chang, W. S.; Tuan, H. Y. Single-Crystalline Copper Nano-Octahedra. *Chem. Mater.* 2015, 27, 8185-8188.
(8) Ensafi, A. A.; Jafari-Asl, M.; Dorostkar, N.; Ghiaci, M.; Martinez-Huerta, M. V.; Fierro, J. L. G. The Fabrication and Characterization of Cu-Nanoparticle Immobilization on a Hybrid Chitosan Derivative-Carbon Support as a Novel Electrochemical Sensor: Application for the Sensitive Enzymeless Oxidation of Glucose and Reduction of Hydrogen Peroxide. *J. Mater. Chem. B* 2014, 2, 706-717.
(9) Tan, Y. W.; Gu, J. J.; Xu, W.; Chen, Z. P.; Liu, D. X.; Liu, Q. L.; Zhang, D. Reduction of CuO Butterfly Wing Scales Generates Cu SERS Substrates for DNA Base Detection. *ACS Appl. Mater. Inter.* 2013, 5, 9878-9882.
(10) Muniz-Miranda, M.; Gellini, C.; Giorgetti, E. Surface-Enhanced Raman Scattering from Copper Nanoparticles Obtained by Laser Ablation. *J. Phys. Chem. C* 2011, 115, 5021-5027.
(11) Im, H. G.; Jung, S. H.; Jin, J.; Lee, D.; Lee, J.; Lee, D.; Lee, J. Y.; Kim, I. D.; Bae, B. S. Flexible Transparent Conducting Hybrid Film Using a Surface-Embedded Copper Nanowire Network: A Highly Oxidation-Resistant Copper Nanowire Electrode for Flexible Optoelectronics. *ACS Nano* 2014, 8, 10973-10979.
(12) Li, C. W.; Kanan, M. W. CO2 Reduction at Low Overpotential on Cu Electrodes Resulting from the Reduction of Thick $Cu_2O$ Films. *J. Am. Chem. Soc.* 2012, 134, 7231-7234.
(13) Li, C. W.; Ciston, J.; Kanan, M. W. Electroreduction of Carbon Monoxide to Liquid Fuel on Oxide-Derived Nanocrystalline Copper. *Nature* 2014, 508, 504-507.
(14) Marimuthu, A.; Zhang, J. W.; Linic, S. Tuning Selectivity in Propylene Epoxidation by Plasmon Mediated Photo-Switching of Cu Oxidation State. *Science* 2013, 339, 1590-1593.
(15) McElwee-White, L. Design of Precursors for the CVD of Inorganic Thin Films. *Dalton Trans.* 2006, 5327-5333.
(16) Lim, B. S.; Rahtu, A.; Gordon, R. G. Atomic Layer Deposition of Transition Metals. *Nat. Mater.* 2003, 2, 749-754.
(17) Qiu, J. J.; Wei, W. D. Surface Plasmon-Mediated Photothermal Chemistry. *J. Phys. Chem. C* 2014, 118, 20735-20749.
(18) Qiu, J. J.; Wu, Y. C.; Wang, Y. C.; Engelhard, M. H.; McElwee-White, L.; Wei, W. D. Surface Plasmon Mediated Chemical Solution Deposition of Gold Nanoparticles on a Nanostructured Silver Surface at Room Temperature. *J. Am. Chem. Soc.* 2013, 135, 38-41.
(19) Orendorff, C. J.; Gole, A.; Sau, T. K.; Murphy, C. J. Surface-Enhanced Raman Spectroscopy of Self-Assembled Monolayers: Sandwich Architecture and Nanoparticle Shape Dependence. *Anal. Chem.* 2005, 77, 3261-3266.
(20) Lippard, S. J.; Ucko, D. Transition Metal Borohydride Complexes. II. Th Reaction of Copper(I) Compounds with Boron Hydride Anions. *Inorg. Chem.* 1968, 7, 1051-1056.
(21) Gysling, H. J. Coordination Complexes of Copper(I) Nitrate. *Inorg. Synth.* 1979, 19, 92-97.
(22) Zhang, X. Y.; Zhao, J.; Whitney, A. V.; Elam, J. W.; Van Duyne, R. P. Ultrastable Substrates for Surface-Enhanced Raman Spectroscopy: $Al_2O_3$ overlayers Fabricated by Atomic Layer Deposition Yield Improved Anthrax Biomarker Detection. *J. Am. Chem. Soc.* 2006, 128, 10304-10309.
(23) Richardson, H. H.; Carlson, M. T.; Tandler, P. J.; Hernandez, P.; Govorov, A. O. Experimental and Theoretical Studies of Light-to-Heat Conversion and Collective Heating Effects in Metal Nanoparticle Solutions. *Nano Lett.* 2009, 9, 1139-1146.
(24) Baldwin, C. L.; Bigelow, N. W.; Masiello, D. J. Thermal Signatures of Plasmonic Fano Interferences: Toward the Achievement of Nanolocalized Temperature Manipulation. *J. Phys. Chem. Lett.* 2014, 5, 1347-1354.

(25) Baffou, G.; Quidant, R. Nanoplasmonics for Chemistry. *Chem. Soc. Rev.* 2014, 43, 3898-3907.
(26) Davidson, J. M. Bis(triphenylphosphine)borohydrido-copper(I). *Chem. Ind.* 1964, 2021-2022.
(27) Mcintyre, N. S.; Cook, M. G. X-Ray Photoelectron Studies on Some Oxides and Hydroxides of Cobalt, Nickel, and Copper. *Anal. Chem.* 1975, 47, 2208-2213.
(28) Hernandez, J.; Wrschka, P.; Oehrlein, G. S. Surface Chemistry Studies of Copper Chemical Mechanical Planarization. *J. Electrochem. Soc.* 2001, 148, G389-G397.
(29) DuChene, J. S.; Williams, B. P.; Johnston-Peck, A. C.; Qiu, J. J.; Gomes, M.; Amilhau, M.; Bejleri, D.; Weng, J. N.; Su, D.; Huo, F. W. et al. Elucidating the Sole Contribution from Electromagnetic Near-Fields in Plasmon-Enhanced $Cu_2O$ Photocathodes. *Adv. Energy Mater.* 2015, DOI: 10.1002/aenm.201501250.
(30) Nainan, K. C.; E., R. G. A New Synthesis of Amine- and Phosphine-Boranes. *Inorg. Chem.* 1969, 8, 2671-2674.
(31) Gawande, M. B.; Goswami, A.; Felpin, F.-X.; Asefa, T.; Huang, X.; Silva, R.; Zou, X.; Zboril, R.; Varma, R. S. Cu and Cu-Based Nanoparticles: Synthesis and Applications in Catalysis. *Chem. Rev.* 2016, 116, 3722-3811.
(32) Yang, Y.; Liu, J. Y.; Fu, Z. W.; Qin, D. Galvanic Replacement-Free Deposition of Au on Ag for Core-Shell Nanocubes with Enhanced Chemical Stability and SERS Activity. *J. Am. Chem. Soc.* 2014, 136, 8153-8156.
(33) Madiyar, F. R.; Bhana, S.; Swisher, L. Z.; Culbertson, C. T.; Huang, X. H.; Li, J. Integration of a Nanostructured Dielectrophoretic Device and a Surface-Enhanced Raman Probe for Highly Sensitive Rapid Bacteria Detection. *Nanoscale* 2015, 7, 3726-3736.
(34) Govorov, A. O.; Zhang, W.; Skeini, T.; Richardson, H.; Lee, J.; Kotov, N. A. Gold Nanoparticle Ensembles as Heaters and Actuators: Melting and Collective Plasmon Resonances. *Nanoscale Res. Lett.* 2006, 1, 84-90.
(35) Williamson, M. J.; Tromp, R. M.; Vereecken, P. M.; Hull, R.; Ross, F. M. Dynamic Microscopy of Nanoscale Cluster Growth at the Solid-Liquid Interface. *Nat. Mater.* 2003, 2, 532-536.
(36) Bocquet, F.; Maurel, C.; Roussel, J. M.; Abe, M.; Koudia, M.; Porte, L. Segregation-Mediated Capping of Volmer-Weber Cu Islands Grown onto Ag(111). *Phys. Rev. B* 2005, 71.
(37) Nilsing, M.; Persson, P.; Ojamae, L. Anchor Group Influence on Molecule-Metal Oxide Interfaces: Periodic Hybrid DFT Study of Pyridine Bound to TiO2 via Carboxylic and Phosphonic Acid. *Chem. Phys. Lett.* 2005, 415, 375-380.
(38) Michota, A.; Bukowska, J. Surface-Enhanced Raman Scattering (SERS) of 4-Mercaptobenzoic Acid on Silver and Gold Substrates. *J. Raman Spectrosc.* 2003, 34, 21-25.
(39) Wei, W.; Li, S. Z.; Qin, L. D.; Xue, C.; Millstone, J. E.; Xu, X. Y.; Schatz, G. C.; Mirkin, C. A. Surface Plasmon-Mediated Energy Transfer in Heterogap Au—Ag Nanowires. *Nano Lett.* 2008, 8, 3446-3449.
(40) Aronoff, Y. G.; Chen, B.; Lu, G.; Seto, C.; Schwartz, J.; Bernasek, S. Stabilization of Self-Assembled Monolayers of Carboxylic Acids on Native Oxides of Metals. *J. Am. Chem. Soc.* 1997, 119, 259-262.
(41) Jiang, L.; You, T. T.; Yin, P. G.; Shang, Y.; Zhang, D. F.; Guo, L.; Yang, S. H. Surface-Enhanced Raman Scattering Spectra of Adsorbates on $Cu_2O$ Nanospheres: Charge-Transfer and Electromagnetic Enhancement. *Nanoscale* 2013, 5, 2784-2789.

Example 2

Surface Enhanced Raman Scattering (SERS) Investigations

The sensing capability of the AgFON substrate after Cu nanoparticle deposition was tested via SERS. The AgFON/Cu hybrid substrate shown in FIG. 3A (5-minute deposition under 2.8 W/cm$^2$ excitation) was immersed in a 1 mM methanol solution of 4-mercaptobenzoic acid (4-MBA) for 20 h and was then gently rinsed with pure methanol. The 4-MBA modified substrates were subsequently dried under a stream of $N_2$. The high chemical affinity of the carboxylate groups ($COO^-$) of MBA for metal oxide surfaces ensures the chemisorption of MBA on the AgFON/Cu substrate to form a monolayer of Raman probe molecules.

The Raman spectrum of 4-MBA adsorbed on AgFON/Cu surface was recorded with a confocal Raman microscope (Horiba micro-Raman spectrometer) equipped with a 100× microscope objective (NA=0.9). The number of gratings in the Raman spectrometer was 1800 grooves/mm. Substrates were excited using a 532 nm laser with a power of 0.6 mW. The Raman spectra were collected through a confocal pinhole of 150 μm using a 2 s acquisition time. The Raman spectrum of the 4-MBA powder was collected with a 50× microscope objective (NA=0.75) with a 532 nm laser at 0.6 mW for 3 s. Characteristic Raman peaks of 4-MBA at 1084 cm$^{-1}$ and 1586 cm$^{-1}$ are the most prominent and known to be enhanced mainly by the local electromagnetic fields from a plasmonic substrate.[1,2] These two peaks were therefore used to determine the Raman enhancement factor (EF) of the AgFON/Cu substrate through the following equation:

$$EF = \frac{I_{surf}/N_{surf}}{I_{bulk}/N_{bulk}} \quad (1)$$

where $I_{surf}$ $I_{bulk}$ and denote the intensities for the aromatic breathing mode at approximately 1586 cm$^{-1}$ of adsorbed 4-MBA on $Cu_2O$ and 4-MBA in the bulk, respectively. $N_{surf}$ and $N_{bulk}$ represent the number of 4-MBA molecules adsorbed on the $Cu_2O$ surface and those present in the bulk, respectively.

We estimated the sampling volume from which the Raman spectrum of 4-MBA powder was obtained by multiplying the area of the laser spot (~2 μm in diameter) and the penetration depth (~1 μm) of the focused beam calculated from 1.22λ/NA. Since the density of 4-MBA was 1.5 g/cm$^3$ and its molecular weight is 154.19 g/mol, the number of 4-MBA molecules $N_{bulk}$ effectively excited by the laser beam was calculated to be 1.65×10$^{10}$. The number of 4-MBA molecules adsorbed on the surface ($N_{surf}$) was estimated according to the equation:

$$N_{surf} = \text{packing density} \times S \quad (2)$$

$$S = [2\pi(r+h)/2\sqrt{3}]r \quad (3)$$

where S is the surface area, r is the radius of the $SiO_2$ sphere, and h is the thickness of the film. The total film thickness is 210 nm. The packing density of adsorbed 4-MBA molecules in a self-assembled monolayer is ca. 4.6×10$^{14}$/cm$^2$.[3] Accordingly, the total number of molecules sampled in the SERS experiments using the AgFON/Cu NP film substrate was ca. 4.6×10$^5$. On the basis of the intensities of the peaks at 1084 cm$^{-1}$ and 1586 cm$^{-1}$, the EFs were estimated to be ~10$^5$ by substituting the appropriate values into equation (1).

Example 2 References (1) Jiang, L.; You, T. T.; Yin, P. G.; Shang, Y.; Zhang, D. F.; Guo, L.; Yang, S. H. Surface-Enhanced Raman Scattering Spectra of Adsorbates on Cu$_2$O Nanospheres: Charge-Transfer and Electromagnetic Enhancement. *Nanoscale* 2013, 5, 2784-2789.

(2) Michota, A.; Bukowska, J. Surface-Enhanced Raman Scattering (SERS) of 4-Mercaptobenzoic Acid on Silver and Gold Substrates. *J. Raman Spectrosc.* 2003, 34, 21-25.

(3) Ye, W. C.; Chen, Y.; Zhou, F.; Wang, C. M.; Li, Y. M. Fluoride-Assisted Galvanic Replacement Synthesis of Ag and Au Dendrites on Aluminum Foil with Enhanced SERS and Catalytic Activities. *J. Mater. Chem.* 2012, 22, 18327-18334.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A method of forming a hybrid plasmonic structure, comprising:
    exposing a plasmonic substrate to a precursor material;
    irradiating the plasmonic substrate and the precursor material with a light energy; and
    forming metal nanoparticles on the surface of the plasmonic substrate to form the hybrid plasmonic structure, wherein the metal nanoparticle is about 1 to 20 nm in diameter, wherein the metal nanoparticle is not gold nanoparticles, wherein the plasmonic substrate is selected from the group consisting of: CuFON, Cu nanobowl, Cu pyramid, AlFON, Al nanobowl, Al pyramid, and Ag pyramid.

2. The method of claim 1, wherein the metal nanoparticle is selected from the group consisting of: a Pt nanoparticle, a Pd nanoparticle, a Fe nanoparticle, a Ti nanoparticle, and a combination thereof.

3. The method of claim 1, wherein irradiating includes irradiating with visible light.

4. The method of claim 3, wherein the power density of the visible light is about 1.6 W/cm$^2$ to 2.8 W/cm$^2$.

5. The method of claim 1, wherein the duration of irradiation is about 1 to 5 minutes.

6. The method of claim 5, wherein irradiating is performed to form a nanoparticle film on the surface of the plasmonic substrate.

7. The method of claim 6, wherein the nanoparticle film has a thickness of about 20 to 80 nm.

8. The method of claim 1, wherein the metal nanoparticle is a Cu nanoparticle.

9. A composition comprising:
    a plasmonic structure including a plasmonic substrate having nanoparticles disposed on the surface of the plasmonic substrate, wherein the nanoparticle is about 1 to 20 nm in diameter, wherein the nanoparticle is not gold nanoparticles, wherein the plasmonic substrate is selected from the group consisting of: CuFON, Cu nanobowl, Cu pyramid, AlFON, Al nanobowl, Al pyramid, and Ag pyramid.

10. The composition of claim 9, wherein the nanoparticle is a metal nanoparticle.

11. The composition of claim 9, further comprising a probe attached to the nanoparticle by a carboxylic acid moiety.

12. The composition of claim 11, wherein the probe is a Raman probe molecule.

13. The composition of claim 9, wherein the metal nanoparticle is a Cu nanoparticle.

* * * * *